United States Patent
Hwang

(10) Patent No.: US 9,637,438 B2
(45) Date of Patent: May 2, 2017

(54) PREPARATION METHOD OF CARBOXYLIC ACIDS OR KETONES USING OZONE, SINGLET STATE-OXYGEN ATOM OR HYDROXYL FREE RADICAL

(71) Applicant: NATIONAL TSING HUA UNIVERSITY, Hsinchu (TW)

(72) Inventor: Kuo-Chu Hwang, Tainan (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 14/818,139

(22) Filed: Aug. 4, 2015

(65) Prior Publication Data

US 2016/0102038 A1 Apr. 14, 2016

(30) Foreign Application Priority Data

Oct. 13, 2014 (TW) .............................. 103135381 A

(51) Int. Cl.
*C07C 51/34* (2006.01)
*B01J 19/12* (2006.01)
*C07C 45/40* (2006.01)

(52) U.S. Cl.
CPC .............. *C07C 51/34* (2013.01); *B01J 19/123* (2013.01); *C07C 45/40* (2013.01)

(58) Field of Classification Search
CPC ......... B01J 19/123; C07C 45/40; C07C 51/34
See application file for complete search history.

(56) References Cited

U.S. PATENT DOCUMENTS

2003/0216577 A1 11/2003 Jary et al.

FOREIGN PATENT DOCUMENTS

EP 0459861 * 4/1991
WO WO 02/096849 A1 12/2002

OTHER PUBLICATIONS

English translation of EP0459861, pp. 1-8, 1991.*
Georgiev et al., "Kinetics and Mechansim of Ozonation of Saturated Hydrocarbons in Solution," Oxidation Communications 31, No. 1, 151-159 (2008).*

* cited by examiner

*Primary Examiner* — Paul A Zucker
*Assistant Examiner* — Mark Luderer
(74) *Attorney, Agent, or Firm* — Muncy, Geissler, Olds & Lowe, P.C.

(57) ABSTRACT

A preparation method of carboxylic acids or ketones using ozone, singlet state oxygen atom $O(^1D)$ or hydroxyl free radical is provided. The method includes: filling ozone, singlet state oxygen atom $O(^1D)$ and/or hydroxyl free radical to cycloalkanes or benzenes at a pre-determined temperature and a pre-determined pressure in the presence or absence of light irradiation to produce carboxylic acids or ketones. The reaction occurs at room temperature and atmospheric pressure without producing harmful side products. The preparation method is a simple, low energy consuming, and eco-friendly method.

12 Claims, 1 Drawing Sheet

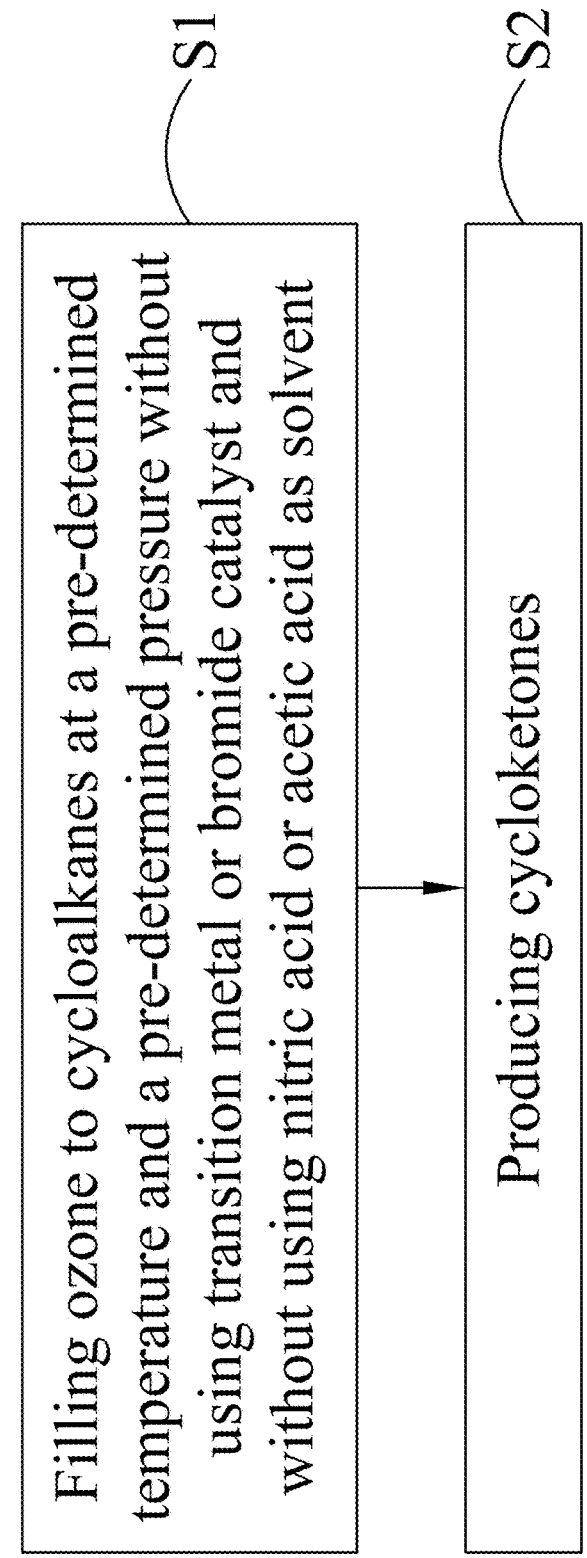

PREPARATION METHOD OF CARBOXYLIC ACIDS OR KETONES USING OZONE, SINGLET STATE-OXYGEN ATOM OR HYDROXYL FREE RADICAL

CROSS-REFERENCE TO RELATED APPLICATION

This application claims priority from Taiwan Patent Application No. 103135381, filed on Oct. 13, 2014, in the Taiwan Intellectual Property Office, the contents of which are hereby incorporated by reference in their entirety for all purposes.

BACKGROUND OF THE INVENTION

1. Field of the Invention

The disclosure relates to a preparation method of carboxylic acids or ketones using ozone, singlet state-oxygen atom or hydroxyl free radical, and more particularly, to a preparation method of carboxylic acids or ketones using ozone in the dark or under uv light irradiation.

2. Description of the Related Art

As far as plastic industry is concerned, adipic acid and terephthalic acid have been playing critical roles. Adipic acid is a precursor for preparation of nylon; and terephthalic acid can be used to prepare polyethylene terephthalate (PET). In the food processing industry, benzoic acid is served as an additive. Methods for mass production of adipic acid, terephthalic acid and benzoic acid in the current industry are, respectively, to oxidize cyclohexane, p-xylene, and toluene at high temperature and high pressure; and the details can be, respectively, referred to parts (a), (b) and (c) in the Reaction 1.

Reaction 1

(a) Adipic acid: Industrial nitric acid oxidation process (3.8 million tones/year)

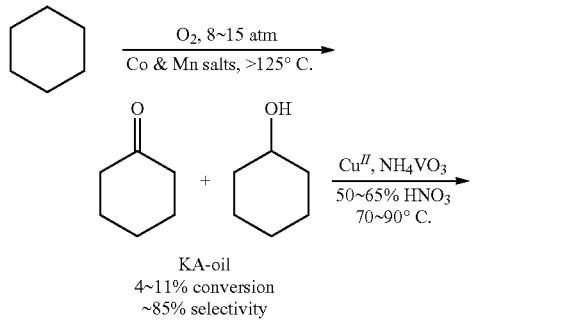

b) Terephthalic acid: AMOCO process (44 million tones/year)

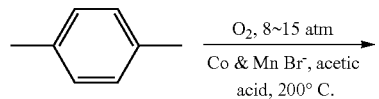

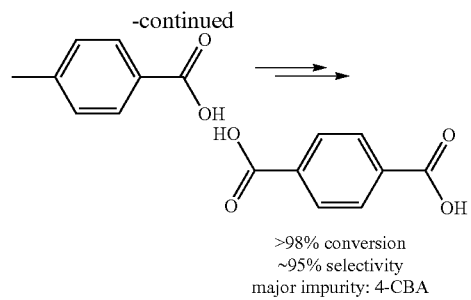

(c) Benzoic acid (0.7 million tons/year)

As shown in part (a) of the Reaction 1, the preparation of adipic acid is by oxidizing cyclohexane using oxygen at a temperature of higher than 125° C. and at a high pressure in the range of 8 to 15 atm in the presence of catalysts, such as, cobalt and manganese, to produce cyclohexanone and cyclohexanol (the so-called "KA" oil), followed by nitric acid (50% to 65%) oxidation to produce adipic acid at temperatures in the range of 70~90° C. By means of the aforementioned method, the conversion and selectivity are good, though, a side product, $N_2O$, is produced. $N_2O$ not only can cause global warming, but also can destruct the ozone layer. Production of 1 kg adipic acid is accompanied with the formation of 0.3 kg of $N_2O$. It is troublesome and energy-consuming to recycle $N_2O$ gas, and to avoid direct release to the atmosphere. In addition, the harsh condition of high temperature and high pressure for the Reaction 1 is highly energy-demanding. Moreover, the use of corrosive nitric acid can only be done in expensive titanium reaction vessels, and the operation thereof may be dangerous to the personnel, who is running the reaction.

As shown in the part (b) of the Reaction 1, preparation of terephthalic acid is by oxidizing p-xylene with oxygen at a high temperature of 200° C. and a high pressure of 8 to 15 atm using catalysts, such as, cobalt and manganese along with bromide ions in acetic acid; and the reaction is progressed by multiple steps to produce terephthalic acid. The preparation of terephthalic acid has good conversion and good selectivity. Owing to the high temperature and high pressure, the industrial terephthalic acid production process is also high energy demanding (and thus high production cost). In addition, both bromide ions and acetic acid are corrosive at high temperatures. The primary impurity, 4-carboxybenzaldehyde (4-CBA), is an inhibitor in the latter polyethylene terephthalate (PET) polymerization process, and has to be removed from the terephthalic acid product. Part (c) of the Reaction 1 is akin to the part (b). The preparation of benzoic acid is to oxidize toluene using oxygen (air) at a high temperature and a high pressure in the presence of catalysts, such as, cobalt and manganese along with bromide ions in acetic acid. Consequently, it is also high energy demanding and environmentally unfriendly.

Inasmuch as the preceding technical problems, the scientific community has been seeking for alternatives. In 1994, the preparation of adipic acid by enzymatic catalysis of glucose was reported, and details can be referred to the Reaction 2 below:

Reaction 2

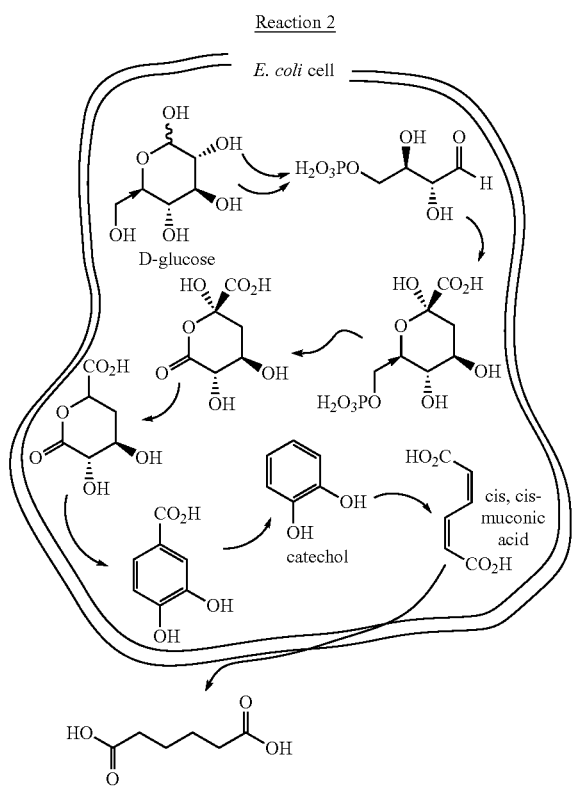

As shown in the Reaction 2, the conversion of glucose to adipic acid was achieved in a biochemistry system (enzymes and reagents are not shown), and the yield is up to 97%. Mass production of adipic acid by the above enzymatic process requires the use of million tons of enzymes, which are not commercial available. This method does not comply with efficiency of manufacturing cost. As a result, this enzymatic reaction is still not able to replace the current industrial production of adipic acid.

In addition, another alternative "green" reaction was reported for the preparation of adipic acid via catalytic oxidation of cyclohexene using hydrogen peroxide ($H_2O_2$) as an oxidant. The details can be referred to the following Reaction 3.

Reaction 3

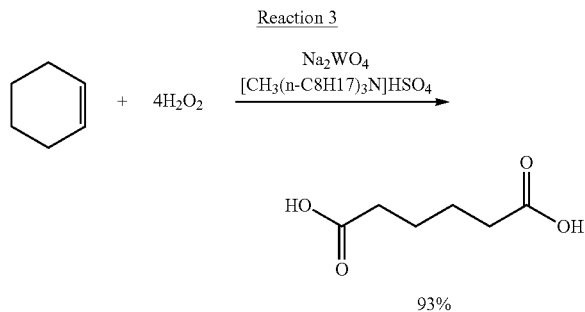

As shown in the Reaction 3, only $H_2O_2$ and water are involved in the reaction, and manufacturing process thereof is very simple and environmentally friendly. However, this cyclohexene-$H_2O_2$ process was not industrialized, since the cost of $H_2O_2$ is higher than the value of adipic acid produced. Overall, 4-4.4 equivalents of $H_2O_2$ was required for production of 1 mole of adipic acid. The price of $H_2O_2$ is ~55% of adipic acid, and thus for the entire reaction, the cost of $H_2O_2$ is ~2.2 times the value of the adipic acid product. Thus, it is economically infeasible. Moreover, cyclohexene is more expensive than cyclohexane. As a result, the reaction is void of industrial applicability.

Because the quantity of the global demand of the adipic acid is ~3.9 million tons/year in 2014, which is equivalent to a market value of about US$ 6.2 billion. In the case of terephthalic acid, the quantity of worldwide annual production is ~44 million tons/year in 2014, which is equivalent to a market value of about US$ 44 billion. In the case of benzoic acid, the quantity of worldwide annual production is ~0.7 million tons/year, which is equivalent to a market value of ~US$ 1.1 billion. Overall, the total market value of adipic acid, terephthalic acid and benzoic acid is about ~51.3 billion USD. Hence, if there is a method being able to improve the preceding problems of the three synthesis methods using the same reaction mechanism, it will benefit the industry a lot and reduce the manufacturing cost greatly at the same time.

SUMMARY OF THE INVENTION

Inasmuch as the aforementioned problems, the purpose of the present invention is to provide a method of preparing carboxylic acids or phenyl ketones using ozone, singlet state-oxygen atom $O(^1D)$ or hydroxyl free radical to resolve the technical problems and high pollution problems involved in the conventional art concerning the harsh conditions, such as, high temperature, high pressure and highly corrosive reaction mediums, required for industrial production of adipic acid, terephthalic acid and benzoic acid.

In accordance with one purpose of the present invention, it provides a method to prepare ketones, which may include steps of: filling at least one of following three oxidants, including ozone, a singlet state-oxygen atom $O(^1D)$, and a hydroxyl free radical to cycloalkanes at a pre-determined temperature and a pre-determined pressure without using transition metal catalysts or bromide catalysts and without using nitric acid or acetic acid as solvent to produce cycloketones; wherein the pre-determined temperature may be in a range between −10° C. and 50° C., and the pre-determined pressure may be in a range between 0.8 atm and 1.2 atm; wherein the cycloalkanes may comprise cyclopentane, cyclohexane, cycloheptane, cyclooctane or a combination thereof; the cycloketones may comprise cyclopentanone, cyclohexanone, cycloheptanone, cyclooctanone or a combination thereof.

Preferably, the singlet state-oxygen atom $O(^1D)$ may be produced by irradiation of ozone by a light beam having a wavelength between 230 nm and 330 nm.

Preferably, the hydroxyl free radical may be produced by reaction of ozone with water, by reaction of a singlet state-oxygen atom $O(^1D)$ with water, by reaction of hydrogen peroxide with ferrous ions, or by reaction of hydrogen peroxide with cuprous ions.

In accordance with another purpose of the present invention, it provides a method to prepare carboxylic acids, which may include steps of: filling at least one of following three oxidants, including ozone, a singlet state-oxygen atom $O(^1D)$, and a hydroxyl free radical to the cycloketones prepared by the method of claim 1 at a second pre-determined temperature and a second pre-determined pressure without using transition metal catalysts or bromide catalysts and without using nitric acid or acetic acid as a solvent to produce aliphatic dicarboxylic acids; wherein the aliphatic dicarboxylic acids may comprise glutaric acid, adipic acid, pimelic acid, suberic acid or a combination thereof.

Preferably, the second pre-determined temperature may be in a range between −10° C. and 50° C., and the second pre-determined pressure may be in a range between 0.8 atm and 1.2 atm; the method may further include a step of adding a co-solvent, and the co-solvent may include at least one component from aluminum oxide, acetonitrile and water.

In accordance with one more purpose of the present invention, it provides a method to prepare aromatic ketones which may include steps of: filling at least one of following three oxidants, including ozone, a singlet state-oxygen atom $O(^1D)$, and a hydroxyl free radical to alkylbenzenes at a pre-determined temperature and a pre-determined pressure without using transition metal catalysts or bromide catalysts and without using nitric acid or acetic acid as a solvent to produce aromatic ketones, wherein an alkyl group of the alkylbenzenes comprises two or more carbon atoms; wherein the alkylbenzenes may include ethyl benzene or diphenylmethane, and the aromatic ketones may include acetophenone or benzophenone.

Preferably, the pre-determined temperature may be in a range between −10° C. and 50° C., and the pre-determined pressure may be in a range between 0.8 atm and 1.2 atm.

Preferably, the singlet state-oxygen atom $O(^1D)$ may be produced by irradiation of ozone by a light beam having a wavelength between 230 nm and 330 nm.

Preferably, the hydroxyl free radical may be produced by reaction of ozone with water, by reaction of a singlet state-oxygen atom $O(^1D)$ with water, by reaction of hydrogen peroxide with ferrous ions, or by reaction of hydrogen peroxide with cuprous ions.

In accordance with another purpose of the present invention, it further provides a method to prepare aromatic carboxylic acids, which may include steps of: filling at least one of following three oxidants, including ozone, a singlet state-oxygen atom $O(^1D)$, and a hydroxyl free radical to benzenes at a pre-determined temperature and a pre-determined pressure without using transition metal catalysts or bromide catalysts and without using nitric acid or acetic acid as solvent to produce aromatic carboxylic acids, wherein the number of carbon atoms of each substituent of the benzenes is 1; wherein the benzenes may comprise toluene, p-xylene, o-xylene, m-xylene, p-toluic acid, 4-carboxybenzaldehyde or a combination thereof; and the aromatic carboxylic acids may comprise benzoic acid, terephthalic acid, phthalic acid, isophthalic acid or a combination thereof.

Preferably, the pre-determined temperature may be in a range between −10° C. and 50° C., and the pre-determined pressure may be in a range between 0.8 atm and 1.2 atm; the method may further comprise a step of adding a co-solvent; and the co-solvent comprises at least one of aluminum oxide, acetonitrile and water.

Preferably, the singlet state-oxygen atom $O(^1D)$ may be produced via irradiation of ozone molecules by a light beam having a wavelength between 230 nm and 330 nm.

Preferably, the hydroxyl free radical may be produced by reaction of ozone with water, by reaction of a singlet state-oxygen atom with water, by reaction of hydrogen peroxide with ferrous ions, or by reaction of hydrogen peroxide with cuprous ions.

According to the preceding descriptions, a method to prepare carboxylic acids or aromatic ketones using ozone, singlet state-oxygen atom or hydroxyl free radical in accordance with the present invention may have one or more advantages as follows:

(1) By means of the method, irradiated-ozone, singlet state-oxygen atom or hydroxyl free radical may be able to react with various kinds of substrates in a closed reactor without limitations of high temperature and pressure and the use of corrosive nitric acid. In addition, production of toxic $N_2O$ can therefore be avoided. As a result, the goals of energy-saving, environmental protection and cost reduction can be accomplished.

(2) By means of the method, ozone may be able to react with various kinds of substrates in normal temperature and pressure in a closed reactor without irradiation, and the process is a simple and convenient manufacturing method.

BRIEF DESCRIPTION OF THE DRAWINGS

The sole FIGURE is a flow chart of a preparation method of carboxylic acids using ozone in accordance with Embodiment 1 of the present invention.

DETAILED DESCRIPTION OF THE PREFERRED EMBODIMENTS

The exemplary embodiments of the present invention will be understood more fully from the detailed description given below and from the accompanying drawings of various embodiments of the invention, which, however, should not be taken to limit the invention to the specific embodiments, but are for explanation and understanding only.

Please refer to the FIGURE, which is a flow chart of the current method to prepare carboxylic acids using ozone in accordance with Embodiment 1 of the present invention. As shown in the FIGURE, a preparation method of carboxylic acids using ozone according to the present invention may include steps of: filling ozone to cycloalkanes or benzenes at a pre-determined temperature and a pre-determined pressure (step S1) to produce aliphatic-dicarboxylic acids or aromatic carboxylic acids (step S2); wherein the cycloalkanes may be selected from the group consisting of cyclopentane, cyclohexane, cycloheptane and cyclooctane, the benzenes may be selected from the group consisting of toluene, p-xylene, o-xylene, m-xylene, p-toluic acid and 4-carboxybenzaldehyde; the aliphatic dicarboxylic acids may be selected from the group consisting of glutaric acid, adipic acid, pimelic acid and suberic acid, and the aromatic carboxylic acids may be selected from the group consisting of benzoic acid, terephthalic acid, phthalic acid and isophthalic acid; and wherein the pre-determined temperature may be in a range between −10° C. and 50° C., and the pre-determined pressure may be in a range between 0.8 atm and 1.2 atm. The reaction can be represented in the following Reaction 4 and Reaction 5.

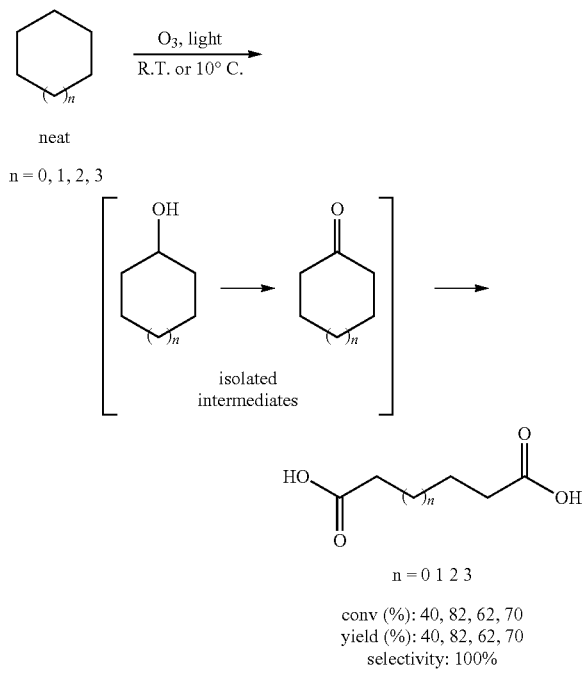

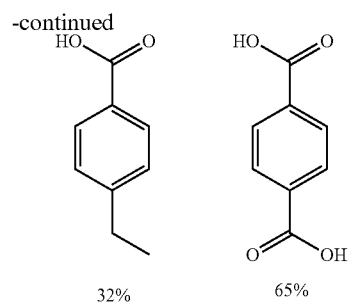

In Embodiment 1, the method further includes a step of adding a co-solvent while p-xylene, o-xylene or m-xylene reacts with ozone; and wherein the co-solvent may include at least one component from aluminum oxide, acetonitrile or water.

In accordance with Embodiment 2 of the present invention, firstly, neat cyclohexane is filled in a glass tube and 20 v/v % of water is added at (dry condition is also allowable) 25° C. and 1 atm, and the opening of the reaction vessel is covered by a lid. Next, the glass tube is exposed to the irradiation from a 100 W Hg lamp, and a plastic pipe is inserted into the glass tube, and ozone is filled continuously through the plastic pipe for about 8 hours. White precipitate is produced gradually, and the crude product of adipic acid is remained in the glass tube when the Hg lamp irradiation stops. The crude product of adipic acid is dispersed in solvents such as ethyl acetate and hexane to become slurry. After shaking for a while, the white precipitate below is pure adipic acid, and conversion and selectivity thereof are 82% and 100%, respectively. Wherein, the conversion indicates a sum of yield of the product and derivatives thereof. The reaction mechanism in accordance with Embodiment 2 is shown in the following Reaction 6.

(i) The reaction of ozone with anhydrous cyclohexane under irradiation.

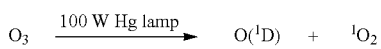

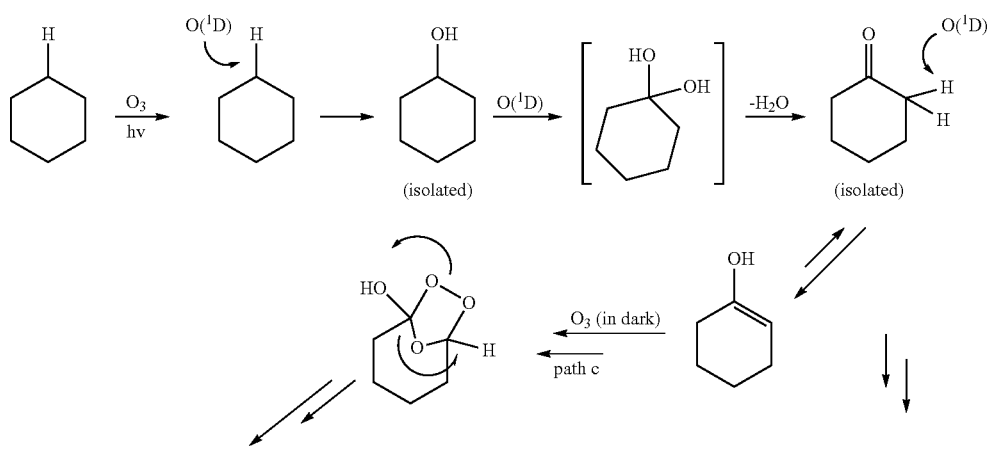

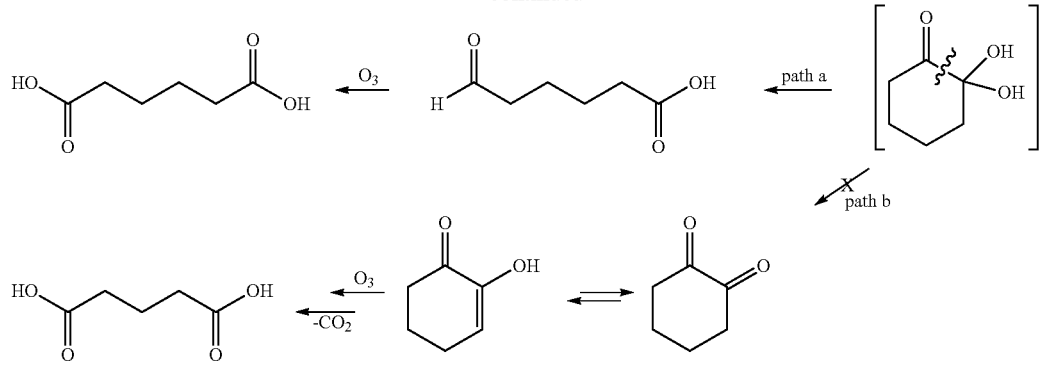

(ii) The reaction of ozone with hydrous cyclohexane under irradiation.

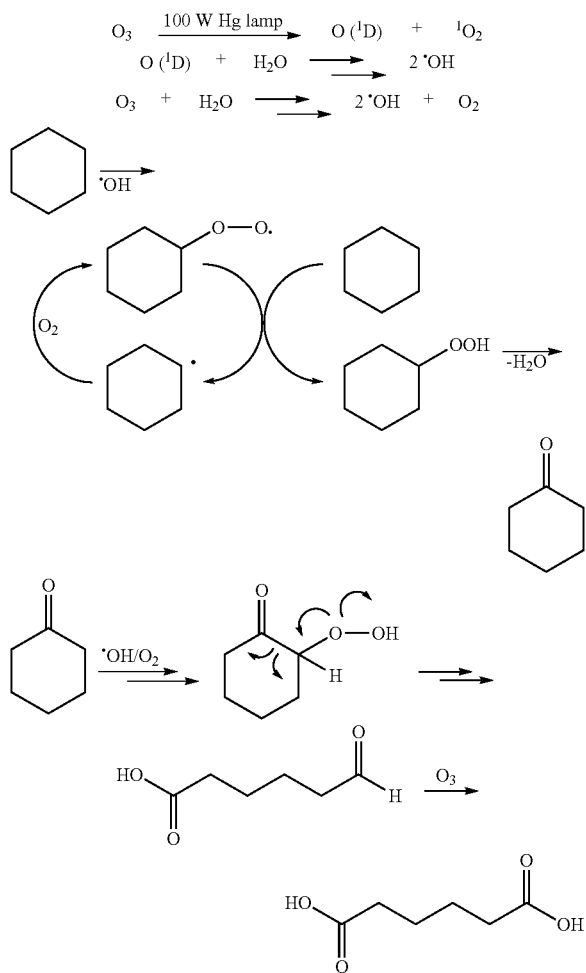

As shown in part (i) of the Reaction 6, when ozone is under irradiation by a 100 W Hg lamp, it produces singlet state-oxygen atom $O(^1D)$. When the $O(^1D)$ reacts with the liquid-phase cyclohexane, the $O(^1D)$ will insert into a C—H bond on the cyclohexane ring to form cyclohexanol; and this reaction is a spontaneous exothermal reaction. The same $O(^1D)$ insertion will occur selectively at the geminal C—H bond to the hydroxyl group to form a geminal diol, which will rapidly undergo dehydration to form cyclohexanone. Afterwards, $O(^1D)$ can further insert into the C—H bond on α carbon of cyclohexanone to form a ketone-hydroperoxide. An O—O bond of the ketone-hydroperoxide breaks, and the electron pair shifts to open ring to produce 6-al-hexanoic acid through the path a. Adipic acid is then formed via further ozone oxidization. The path b is another possible reaction pathway towards producing adipic acid. The reaction of the path b is firstly to form cyclohexanedione. Under the ozone-uv irradiation condition, cyclohexanedione was converted to glutaric acid, instead of adipic acid (see results in Table 1). Therefore, the path b doesn't happen under practical circumstance. It can be observed through what has discussed above that cyclohexanone and cyclohexenol are reversible enol-keto form tautomers. In path c, cyclohexenol can react with ozone in the dark to generate adipic acid.

In the presence of water, both ozone and singlet state-oxygen atom $O(^1D)$ can react with water to produce hydroxyl free radical (referring to part (ii) of Reaction 6); and the hydroxyl free radical can react with cyclohexane through a series of peroxidation to produce adipic acid. Here, the hydroxyl free radical may be produced by other reactions, such as, by reaction of $H_2O_2$ with $Fe^{2+}$ or $Cu^+$. As a result, the production of the hydroxyl free radical is not limited to the processes via reactions of ozone or singlet state-oxygen atom $O(^1D)$ with water.

Embodiments 3 to 5, in accordance with the present invention, are akin to the Embodiment 2, and the difference thereof only lies in that cyclopentane, cycloheptane and cyclooctane are, respectively, served reactants; and upon ozone-uv irradiation for 5 hours, these substrates were oxidized and converted to glutaric acid, pimelic acid and suberic acid with yields of 40%, 62% and 70%, respectively.

Please refer to the Reaction 4. The aforementioned Embodiments 2 to 5 all belong to the reaction shown in the Reaction 4. As shown in the Reaction 6 which shows the reaction mechanism of the Embodiment 2, there are many intermediates produced in the process, and these intermediates may also be able to react with singlet state-oxygen atom to produce aliphatic dicarboxylic acids. Therefore, Embodiments 6 to 8 in accordance with the present invention are akin to the Embodiment 2; and the difference thereof only lies in that cyclohexanol, cyclohexanone and cyclohexanedione are, respectively, served reactants; and they react with ozone under irradiation for 5, 5 and 1 hour, respectively, to produce adipic acid, adipic acid and glutaric acid, respectively.

For the sake of clarity, the related reaction conditions and results of Embodiments 2 to 8 in accordance with the present invention are summarized in the Table 1.

TABLE 1

| | Reagent | Products | Reaction Time (Hour) | Yield (%) | Selectivity (%) |
|---|---|---|---|---|---|
| Embodiment 2 |  Cyclohexane | 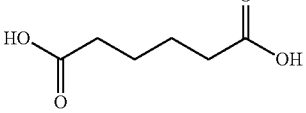 Adipic acid | 8 | 82 | 100 |
| Embodiment 3 |  Cyclopentane | 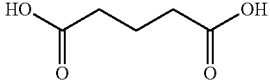 Glutaric acid | 5 | 40 | 100 |
| Embodiment 4 |  Cycloheptane | 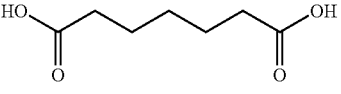 Pimelic acid | 5 | 62 | 100 |
| Embodiment 5 |  Cyclooctane | 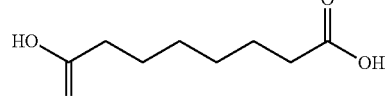 suberic acid | 5 | 70 | 100 |
| Embodiment 6 | 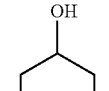 Cyclohexanol | 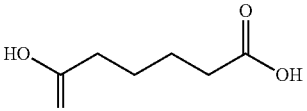 Adipic acid | 5 | 75 | 100 |
| Embodiment 7 | 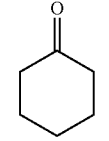 Cyclohexanone | 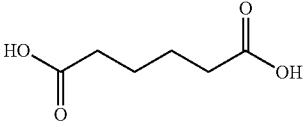 Adipic acid | 5 | 90 | 100 |
| Embodiment 8 | 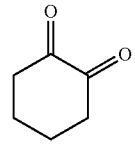 Cyclohexanedione | 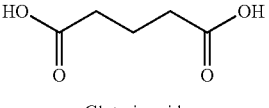 Glutaric acid | 1 | 95 | 100 |

In accordance with the Embodiment 9 of the present invention, firstly, neat p-xylene is filled in a glass tube, and ozone gas flow is introduced to the glass tube for about 10 minutes. The reaction solution was exposed to 100 W Hg lamp light irradiation for about 15 hours. White precipitate is produced gradually. After light irradiation, solvents are added therein to wash away unreacted substrate from the solid precipitate; and the white solid precipitate was collected by either centrifugation or filtration. The white solid is composed of terephthalic acid and p-toluic acid; and the conversion was determined to be ~80 mol %.-Embodiment 9 in accordance with the present invention is shown in the Reaction 5.

Please refer to the Reaction 5, the condition of the Embodiment 9 leads to formation of 20 mol % terephthalic acid and 60 mol % p-toluic acid. Because p-toluic acid does not dissolve in p-xylene and exists in the form of a solid, the poor contact of solid p-toluic acid forbids further oxidative conversion of p-toluic acid to terephthalic acid. Consequently, if increase in the yield of terephthalic acid is expected when a "better" solvent is used to help dissolution of p-toluic acid, which allows p-tuluic acid to be easily accessed by oxidants in the solution. As a result, Embodiments 10 in accordance with the present invention is akin to the Embodiment 9; and the difference thereof only lies in the process of reaction. 45 mol % of terephthalic acid and 45 mol % of p-Toluic acid are, respectively, produced after 10 hours of reaction. Hence, the yield of terephthalic acid is effectively enhanced.

Embodiment 11 in accordance with the present invention is akin to the Embodiment 9; and the difference thereof only lies in the fact that a co-solvent of xylene, acetonitrile and water (in 5:3:2 volume ratio) is used in the reaction, and the pH value is controlled to be ~4.5. The co-solvent is a so-called "green solvent" which is composed of a mixture of several environmentally-friendly solvents; and the purpose of using the co-solvent is to dissolve the otherwise insoluble, reaction intermediate, such as, p-toluic acid, so that further oxidation of p-toluic acid can be proceeded and the yield of the desirable ultimate product, i.e., terephthalic acid, is increased. Hence, in the Embodiment 11 in accordance with the present invention, the p-toluic acid is re-dissolved by the co-solvent to allow further oxidation and the yield of terephthalic acid is effectively promoted up to 65%.

In the Embodiment 11 in accordance with the present invention, even though re-dissolving in the co-solvent of xylene, acetonitrile and water (in 5:3:2 volume ratio), the yield of p-toluic acid is 32%. In addition, another reaction intermediate, i.e., 4-carboxybenzaldehyde (4-CBA), may be detected by NMR spectrum. Hence, Embodiment 12 in accordance with the present invention is to treat 1 M p-toluic acid in an acetonitrile-water co-solvent (in a 2:1 volume ratio) with ozone-uv irradiation for 8 hours, and terephthalic acid is produced with a yield up to 95%. Embodiment 13 in accordance with the present invention is to treat 1 M 4-carboxybenzaldehyde in a acetonitrile-water (in a 2:1 volume ratio) co-solvent with ozone-uv irradiation for 5 hours; and terephthalic acid is produced with a yield up to 98%. As a result, in Embodiment 11, ozone-uv irradiation of a p-xylene-acetonitrile-water (in 5:3:2 volume ratio) solution leads to formation of terephthalic acid with a higher yield of 65%.

Embodiment 14 in accordance with the present invention is to prepare phthalic acid by ozonolysis-uv irradiation of o-xylene; and the reaction thereof is akin to the Embodiment 9. The reaction solution is composed of o-xylene, acetonitrile and water in a 5:3:2 volume ratio with a pH value of ~4.5. The uv light irradiation time is about 20 hours, which leads to formation of 45 mol % phthalic acid and 50 mol % o-toluic acid. The Embodiment 15 is akin to the Embodiment 14, and the difference thereof only lies in that the m-xylene is used as a substrate, where 53 mol % isophthalic acid and 42 mol % m-toluic acid were formed.

The Embodiment 16 in accordance with the present invention is to prepare benzoic acid by ozone-uv irradiation of neat toluene without adding co-solvent, and reaction thereof is akin to the Embodiment 9. After 8 hours of ozone-uv irradiation, 55 mol % of benzoic acid and 5 mol % of benzaldehyde were produced.

For the sake of clarity, the related reaction conditions and results of the Embodiments 9 to 16 in accordance with the present invention are summarized in the following Table 2.

TABLE 2

| | Reagent | Solvent | Products (Yield, %) | By-products (Yield, %) | Reaction Time (Hour) | Selectivity (%) |
|---|---|---|---|---|---|---|
| Embodiment 9 | p-Xylene | — | Terephthalic acid (60%) | p-Toluic acid (60%) | 15 | 80 |
| Embodiment 10 | p-Xylene | γ Al$_2$O$_3$ (25 wt %) | Terephthalic acid (45%) | p-Toluic acid (45%) | 10 | 95 |

TABLE 2-continued

| | Reagent | Solvent | Products (Yield, %) | By-products (Yield, %) | Reaction Time (Hour) | Selectivity (%) |
|---|---|---|---|---|---|---|
| Embodiment 11 | p-Xylene | p-Xylene: acetonitrile: Water = 5:3:2 (pH = 4.5) | Terephthalic acid (65%) | p-Toluic acid (32%) | 20 | 97 |
| Embodiment 12 | p-Toluic acid | Acetonitrile: Water = 2:1 (1M) | Terephthalic acid (95%) | — | 8 | 95 |
| Embodiment 13 | 4-carboxybenzaldehyde | Acetonitrile: Water = 2:1 (1M) | Terephthalic acid (98%) | — | 5 | 98 |
| Embodiment 14 | o-xylene | o-xylene: Acetonitrile: Water = 5:3:2 (pH = 4.5) | Phthalic acid (45%) | o-Toluic acid (50%) | 20 | 95 |
| Embodiment 15 | m-Xylene | m-Xylene: Acetonitrile: Water = 5:3:2 (pH = 4.5) | isophthalic acid (53%) | m-Toluic acid (42%) | 20 | 96 |
| Embodiment 16 | Toluene | — | Benzoic acid (55%) | Benzaldehyde (5%) | 8 | 60 |

In summary, preparation of carboxylic acids by ozone-uv irradiation in accordance with the present invention is expected to greatly reduce the production cost of adipic acid and terephthalic acid; and this method is economically feasible. The present invention is also applicable for preparation of aromatic ketones, albeit their total worldwide annual capacities are not as large as those for adipic acid and terephthalic acid. Aromatic ketones are important intermediates for synthesis of various medicinal molecules used in the pharmaceutical industry; and aromatic ketones are of high prices, thus aromatic ketone absolutely has its applied values. Therefore, the Embodiment 17 in accordance with the present invention is to produce acetophenone with a yield of 75% by ozone treatment and concurrent uv irradiation of neat ethylbenzene. The embodiment 18 is to produce benzophenone with yield of 80% by ozone treatment and concurrent uv irradiation of neat diphenylmethane. The related reaction conditions and results of Embodiments 17 and 18 in accordance with the present invention are summarized in the following Table 3.

TABLE 3

| | Reagent | Products | Reaction Time (Hour) | Yield (%) | Selectivity (%) |
|---|---|---|---|---|---|
| Embodiment 17 | 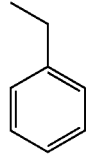 Ethylbenzene | 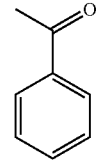 Acetophenone | 8 | 75 | 75 |
| Embodiment 18 | 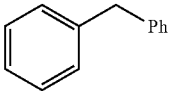 Diphenylmethane | 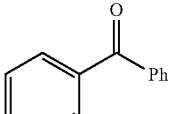 Benzophenone | 8 | 80 | 80 |

The present invention is mainly to prepare singlet state-oxygen atom O($^1$D) by ozone under irradiation, and singlet state-oxygen atom may also be produced by the other gases such as $N_2O$ upon irradiation. However, the singlet state-oxygen atom O($^1$D) produced by irradiation of $N_2O$ has short presence duration and may become triplet state-oxygen atom O($^3$P) soon, so the singlet state-oxygen atom produced by irradiation of $N_2O$ is not be able to carry out the reaction efficiently in accordance with the present invention. Therefore, if the presence duration for singlet state-oxygen atom O($^1$D) used to carry out the reaction is sufficient, the singlet state-oxygen atom can be prepared by any other gases and is not limited to ozone.

On the other hand, the present invention may also only use ozone and substrates to carry out the reaction without additional irradiation, but yield thereof is lower (as compared to the photo-irradiated reaction). The mechanism of the dark reaction is also not the same as that of the photo-irradiated reaction. The mechanism of the dark reaction mainly involves that ozone abstracts a hydrogen atom directly from substrates to produce HOOO. and alkyl (R.) free radicals. The alkyl free radical can further react with molecular oxygen to proceed through a peroxidation chain reaction to generate alkyl hydroperoxide (ROOH). Consequently, the Embodiments 19 to 35 in accordance with the present invention are akin to the Embodiments 2 to 18 which are to use the same reactants, co-solvent; and the reaction time is the same, as well. The difference thereof only lies in that the former is the reaction carried out in the presence of ozone in the dark, and the related reaction conditions and yields of the Embodiments 19 to 35 in accordance with the present invention are summarized in the following Tables 4, 5 and 6.

TABLE 4

| | Reagent | Products | Yield (%) | Selectivity (%) |
|---|---|---|---|---|
| Embodiment 19 | Cyclohexane | Adipic acid | 22 | 100 |
| Embodiment 20 | Cyclopentane | Glutaric acid | 5 | 100 |
| Embodiment 21 | Cycloheptane | Pimelic acid | 10 | 100 |
| Embodiment 22 | Cyclooctane | suberic acid | 13 | 100 |
| Embodiment 23 | Cyclohexanol | Adipic acid | 15 | 100 |
| Embodiment 24 | Cyclohexanone | Adipic acid | 25 | 100 |
| Embodiment 25 | Cyclohexanedione | Glutaric acid | 95 | 100 |

TABLE 5

| | Reagent | Solvent | Products (Yield, %) | By-products (Yield, %) | Reaction Time (Hour) | Selectivity (%) |
|---|---|---|---|---|---|---|
| Embodiment 26 | 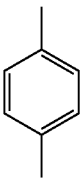 p-Xylene | — | 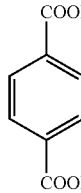 Terephthalic acid (0%) |  p-Toluic acid (30%) | 15 | 80 |
| Embodiment 27 | 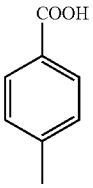 p-Xylene | γ Al$_2$O$_3$ (25 wt %) | 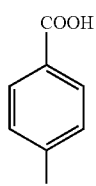 Terephthalic acid (10%) | 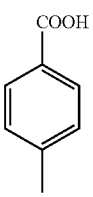 p-Toluic acid (50%) | 10 | 95 |
| Embodiment 28 | 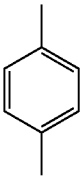 p-Xylene | p-Xylene: acetonitrile: Water = 5:3:2 (pH = 4.5) | 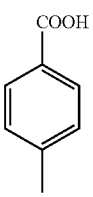 Terephthalic acid (10%) |  p-Toluic acid (30%) | 20 | 97 |
| Embodiment 29 | 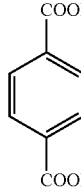 p-Toluic acid | Acetonitrile: Water = 2:1 (1M) | 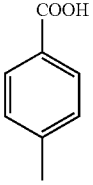 Terephthalic acid (95%) | — | 8 | 95 |
| Embodiment 30 |  4-carboxy-benzaldehyde | Acetonitrile: Water = 2:1 (1M) | 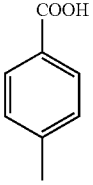 Terephthalic acid (95%) | — | 5 | 98 |

TABLE 5-continued

| | Reagent | Solvent | Products (Yield, %) | By-products (Yield, %) | Reaction Time (Hour) | Selectivity (%) |
|---|---|---|---|---|---|---|
| Embodiment 31 | o-xylene | o-xylene: Acetonitrile: Water = 5:3:2 (pH = 4.5) | Phthalic acid (5%) | o-Toluic acid (30%) | 20 | 95 |
| Embodiment 32 | m-Xylene | m-Xylene: Acetonitrile: Water = 5:3:2 (pH = 4.5) | isophthalic acid (10%) | m-Toluic acid (30%) | 20 | 96 |
| Embodiment 33 | Toluene | — | Benzoic acid (55%) | Benzaldehyde (10%) | 8 | 60 |

TABLE 6

| | Reagent | Products | Reaction Time (Hour) | Yield (%) | Selectivity (%) |
|---|---|---|---|---|---|
| Embodiment 34 | Ethylbenzene | Acetophenone | 8 | 40 | 75 |
| Embodiment 35 | Diphenylmethane | Benzophenone | 8 | 50 | 80 |

In conclusion, a method was invented for preparation of carboxylic acids or ketones using ozone, singlet state-oxygen atom or hydroxyl free radical in accordance with the present invention at normal temperature and pressure without producing global warming and ozone-depleting $N_2O$ gas. This method uses environmentally-friendly solvents, and thus, the method is an energy-saving, and environmentally-friendly process. Particularly, this method is applicable to prepare those important industrial key chemicals of great annual capacities, such as adipic acid, terephthalic acid, benzoic acid, acetophenone, and benzophenone, which are of higher price. As a result, the present invention is expected to be economically feasible in the industry.

While the means of specific embodiments in the present invention has been described by reference drawings, numerous modifications and variations could be made thereto by those skilled in the art without departing from the scope and the spirit of the invention set forth in the claims. The modifications and variations should not be limited by the specification of the present invention.

What is claimed is:

1. A method for preparation of ketones, comprising steps of:
   providing an oxidant comprising at least one of a singlet state-oxygen atom $O(^1D)$ and a hydroxyl free radical; and
   reacting the oxidant and cycloalkanes at a pre-determined temperature and a pre-determined pressure without using transition metal catalysts or bromide catalysts and without using nitric acid or acetic acid as a solvent to produce cycloketones; wherein the pre-determined temperature is in a range between −10° C. and 50° C., and the pre-determined pressure is in a range between 0.8 atm and 1.2 atm;
   wherein the cycloalkanes comprise cyclopentane, cyclohexane, cycloheptane, cyclooctane or a combination thereof; the cycloketones comprise cyclopentanone, cyclohexanone, cycloheptanone, cyclooctanone or a combination thereof.

2. The method of claim 1, wherein the singlet state-oxygen atom $O(^1D)$ is produced by irradiation of ozone by a light beam having a wavelength between 230 nm and 330 nm.

3. The method of claim 1, wherein the hydroxyl free radical is produced by reaction of ozone with water, by reaction of a singlet state-oxygen atom $O(^1D)$ with water, by reaction of hydrogen peroxide with ferrous ions, or by reaction of hydrogen peroxide with cuprous ions.

4. A method for preparation of carboxylic acids, comprising steps of:
   providing an oxidant comprising at least one of ozone, a singlet state-oxygen atom $O(^1D)$, and a hydroxyl free radical; and
   reacting the oxidant and the cycloketones prepared by the method of claim 1 at a second pre-determined temperature and a second pre-determined pressure without using transition metal catalysts or bromide catalysts and without using nitric acid or acetic acid as a solvent to produce aliphatic dicarboxylic acids,
   wherein the aliphatic dicarboxylic acids comprise glutaric acid, adipic acid, pimelic acid, suberic acid or a combination thereof.

5. The method of claim 4, wherein the second pre-determined temperature is in a range between −10° C. and 50° C., and the second pre-determined pressure is in a range between 0.8 atm and 1.2 atm;
   wherein the method further comprises a step of adding a co-solvent, and
   the co-solvent comprises at least one of aluminum oxide, acetonitrile and water.

6. A method for preparation of aromatic ketones, comprising steps of:
   providing an oxidant comprising at least one of ozone, a singlet state-oxygen atom $O(^1D)$ and a hydroxyl free radical produced by reaction of ozone with water, or by reaction of a singlet state-oxygen atom $O(^1D)$ with water; and
   reacting the oxidant and alkylbenzenes at a pre-determined temperature and a pre-determined pressure without using transition metal catalysts or bromide catalysts and without using nitric acid or acetic acid as a solvent to produce aromatic ketones, wherein an alkyl group of the alkylbenzenes comprises two or more carbon atoms;
   wherein the alkylbenzenes comprise ethyl benzene or diphenylmethane; and the aromatic ketones comprise acetophenone or benzophenone.

7. The method of claim 6, wherein the pre-determined temperature is in a range between −10° C. and 50° C., and the pre-determined pressure is in a range between 0.8 atm and 1.2 atm.

8. The method of claim 6, wherein the singlet state-oxygen atom $O(^1D)$ is produced by irradiation of ozone by a light beam having a wavelength between 230 nm and 330 nm.

9. A method for preparation of aromatic carboxylic acids, comprising steps of:
   providing an oxidant comprising at least one of ozone, a singlet state-oxygen atom $O(^1D)$, and a hydroxyl free radical; and
   reacting the oxidant and benzenes at a pre-determined temperature and a pre-determined pressure without using transition metal catalysts or bromide catalysts and without using nitric acid or acetic acid as a solvent to produce aromatic carboxylic acids, wherein the number of carbon atoms of each substituent of the benzenes is 1;
   wherein the benzenes comprise toluene, p-xylene, o-xylene, m-xylene, p-toluic acid, 4-carboxybenzaldehyde or a combination thereof; and the aromatic carboxylic acids comprise benzoic acid, terephthalic acid, phthalic acid, isophthalic acid or a combination thereof.

10. The method of claim 9, wherein the pre-determined temperature is in a range between −10° C. and 50° C., and the pre-determined pressure is in a range between 0.8 atm and 1.2 atm;
    wherein the method further comprises a step of adding a co-solvent; and
    the co-solvent comprises at least one of aluminum oxide, acetonitrile and water.

11. The method of claim 9, wherein the singlet state-oxygen atom $O(^1D)$ is produced by irradiation of ozone by a light beam having a wavelength between 230 nm and 330 nm.

12. The method of claim 9, wherein the hydroxyl free radical is produced by reaction of ozone with water, by reaction of a singlet state-oxygen atom $O(^1D)$ with water, by reaction of hydrogen peroxide with ferrous ions, or by reaction of hydrogen peroxide with cuprous ions.

* * * * *